(12) United States Patent
Hussain et al.

(10) Patent No.: US 11,543,354 B2
(45) Date of Patent: Jan. 3, 2023

(54) QUANTITATIVE DETECTION OF NON-FLUORINE ANTI-SOIL USING A FLUORESCENT TRACE INDICATOR

(71) Applicant: TARKETT USA INC., Solon, OH (US)

(72) Inventors: Maqbool Hussain, Marietta, GA (US); David Wilkinson, Dalton, GA (US)

(73) Assignee: TARKETT USA INC., Solon, OH (US)

( * ) Notice: Subject to any disclaimer, the term of this patent is extended or adjusted under 35 U.S.C. 154(b) by 353 days.

(21) Appl. No.: 16/842,094

(22) Filed: Apr. 7, 2020

(65) Prior Publication Data

US 2020/0326280 A1    Oct. 15, 2020

Related U.S. Application Data

(60) Provisional application No. 62/834,045, filed on Apr. 15, 2019.

(51) Int. Cl.
| | | |
|---|---|---|
| G01N 21/64 | (2006.01) | |
| G01N 1/28 | (2006.01) | |
| C07C 317/14 | (2006.01) | |
| G01N 33/36 | (2006.01) | |
| G01N 1/38 | (2006.01) | |

(52) U.S. Cl.
CPC ......... G01N 21/645 (2013.01); C07C 317/14 (2013.01); G01N 1/28 (2013.01); G01N 21/643 (2013.01); G01N 33/36 (2013.01); D06M 2200/01 (2013.01); G01N 2001/388 (2013.01)

(58) Field of Classification Search
CPC ...... G01N 1/28; G01N 21/643; G01N 21/645; G01N 33/36; G01N 2001/388; C07C 317/14; D06M 2200/01
See application file for complete search history.

(56) References Cited

U.S. PATENT DOCUMENTS

| | | | |
|---|---|---|---|
| 4,783,314 A * | 11/1988 | Hoots ..................... | G01F 1/704 422/62 |
| 5,413,719 A | 5/1995 | Sivakumar | |
| 5,702,684 A | 12/1997 | McCoy | |
| 6,727,071 B1 * | 4/2004 | Dunlay .................. | B82Y 30/00 435/375 |
| 7,910,371 B2 | 3/2011 | Johnson | |
| 8,927,052 B2 | 1/2015 | Dubreuil | |
| 2006/0275881 A1 * | 12/2006 | Qi ............................ | C12P 7/40 435/254.2 |
| 2010/0183584 A1 * | 7/2010 | Slepak ............... | G01N 33/6893 514/21.4 |

(Continued)

*Primary Examiner* — Sang H Nguyen
(74) *Attorney, Agent, or Firm* — Norris McLaughlin, P.A.

(57) ABSTRACT

A method for quantitatively and indirectly measuring non-fluorine anti-soil chemistry in carpet applications, is based on a known amount of FI trace to be added along with anti-soil chemistry in formulation prior to application to a carpet surface. The anti-soil chemistry with the trace amount of FI is then applied to the carpet through a topical foam or spray applicator during a precoating process. After completion of the precoat process, a carpet sample is collected, carpet face fiber is shaved, and FI is extracted using water. The extracted water solution is used to measure the fluorescence intensity (in counts per second or "CPS") using a Fluorimeter.

9 Claims, 5 Drawing Sheets

(56) References Cited

U.S. PATENT DOCUMENTS

2011/0306082 A1* 12/2011 Gee ................... G01N 21/75
　　　　　　　　　　　　　　　　　　　　　　　　546/10
2012/0196375 A1　　8/2012 Granja et al.
2014/0370251 A1　12/2014 Bumpus et al.
2016/0205946 A1* 7/2016 Stauffer ............... A61L 2/232
2019/0307924 A1* 10/2019 Stevenson ........... A61L 31/129

* cited by examiner

Emission spectrum of pure fluorescent trace indictor sample in deionized water at a concentration of 10 ppm.

QUANTITATIVE DETECTION OF NON-FLUORINE ANTI-SOIL USING A FLUORESCENT TRACE INDICATOR

FIELD OF THE INVENTION

Disclosed herein is a test method for quantitatively measuring non-fluorine anti-soil chemistry used in textile, e.g., carpet applications.

DISCUSSION AND COMPARISON WITH RELEVANT ART

It is known to treat textile fabrics such as wovens, knits or nonwovens with treatments, often in the form of aqueous dispersions, to endow the fabrics with desired properties. One treatment for textiles provides anti-soil properties. It is further known in the relevant industry to use fluorinated anti-soil in carpet applications. Associated fluorine elemental test method to monitor the application rate and quality control of use of said fluorinated anti-soil had been developed. However, it would be preferable to eliminate fluorine anti-soil chemistry and replace it with eco-friendly non-fluorine anti-soil such as Eco-Ensure™ anti-soil topical treatment to protect carpet face-fiber from soiling and staining (available from Tarkett, Eco-Ensure™ is designed as a water-based, non-fluorinated, anti-soil chemistry. The proprietary Eco-Ensure™ treatment is applied through a heat and force actuated cohesion process that results in mechanical polymer entrapment and complete coverage of all individual fiber surfaces of carpet products.) One issue with the use of such non-fluorine anti-soil includes the lack of a test method to monitor and measure its application level on carpet.

To address this problem, the inventors have developed a novel, cost-effective, quantitative test method that can be used to measure non-fluorine anti-soil chemistry in carpet applications and lead to a uniform process and provide better quality control. This method will allow for detection and monitoring of the anti-soil application rate with more consistency. In addition, this method can be used beyond Eco-Ensure application and testing. For instance, it can be used with a manufacturing process, such as material coating or compounding, where the material application rate cannot otherwise be measured and monitored directly using the processing materials. According to the inventive test method as described herein, addition of a trace amount of a fluorescent indicator (FI) to the processing material formulation will allow indirect measuring and monitoring of the application rate of the materials. The FI provides emission in the non-visible UV-region and will not impact the carpet color aesthetics. The florescence from trace indicator is not visible to the human eye as FI provides emission in the non-visible UV-region, having emission maximum at around 334 nm.

U.S. Pat. No. 8,927,052 issued to Dubreuil teaches a method for characterizing deposit of a plasma coating on a substrate. Dubreuil's deposit comprises a coating precursor and a fluorophore compound. Dubreuil's method is particularly directed to a continuous, in-line deposit of a coating layer, and downstream in a continuous, in-line fashion, exciting the fluorophore to emit fluorescent light. By observing the relative level of fluorescence along the substrate, one can determine the approximate coating thickness as well as the homogeneity of the applied layer.

Unlike the inventive process described herein, Dubreuil does not discuss a batch measuring process and also does not contemplate that the retained amount of coating as applied is to be measured. While not explicitly stated, this is seemingly because the substrate is itself smooth and the coating would be fully applied. While levels of thickness of the coating may vary because of process limitations, it is not foreseen that the amount of coating, on average, would be less than the intended amount.

In contrast, in the inventive process described herein, the substrate on which the coating is applied is an irregular, three-dimensional textile. The coating is applied by spraying or using a foam applicator. Because of the surface material, irregular shape, and spraying application, it may be the case that the coating is not applied and retained on the substrate at the level intended. Likewise, visual inspection of the thickness or homogeneity of the applied chemistry is not possible because of the nature of the carpet surface.

Accordingly, the skilled person would not readily transfer the in-line observation of fluorescence to the problem of coating retention on a carpet surface. There is no suggestion in Dubreuil of applying the coating, then shaving off a sample, extracting the FI in water, and measuring the actual fluorescence against the expected fluorescence in order to indirectly measure the degree of retention of the anti-soil coating.

U.S. Patent Application Publication No. 2014/0370251 by Bumpus teaches a flame-retardant identification system for textiles based on a fluorescent tracing and tagging compound. This is specifically directed to textiles having applied thereon a flame-retardant coating. An 'invisible' marking stamp comprising certification data is applied to the textile, so that the stamp is visible only under an ultra-violet light source. Upon laundering, both the coating and the stamp may eventually wash off, rendering the textile no longer flame retardant. The visibility of the stamp is thus indirectly indicating the continued presence of the flame-retardant coating. However, in contrast to the inventive process described herein, Bumpus applies the FI as a single, localized tag, and the fluorescence is measured only in a qualitative fashion after production of the product is complete, and then laundered. Unlike the inventive test method described herein, Bumpus does not relate to measuring the degree of application of a coating in a quantitative fashion as a test of the manufacturing process itself.

U.S. Pat. No. 7,910,371 issued to Johnson teaches a method of monitoring residual treating agent in treated water wherein fluorescent tracers are used to indirectly determine the concentration of remaining treating agent in the water. The resulting continuous measurement is used to control the treating dosage. However, in Johnson's method, the fluorescence level is measured directly and continuously in a downstream water sample. Similarly, U.S. Pat. No. 5,702,684 issued to McCoy and U.S. Pat. No. 5,413,719 issued to Sivakumar both teach use of FI additive to indirectly measure the degree of presence of an agent in a fluid system. In contrast, the inventive process described herein requires that a sample of the solid substrate be taken, and then the FI is dissolved out into water, before fluorescence of the water solution is measured in batch fashion.

Finally, U.S. Patent Application Publication No. 2012/0196375 by Granja relates to use of FI materials for detecting and visualizing organic laundry soils and determining the cleaning efficacy of a laundry product. Here the FI indicates directly the presence of a soil material under UV light, where the solid material is not visible to the naked eye. Granja is not related to using FI as an indirect indicator of the quantitative presence of a chemical layer on a substrate.

These and further aspects of the invention will be understood with reference to the following specification and drawings.

SUMMARY OF THE INVENTION

A method has been developed for quantitatively and indirectly measuring non-fluorine anti-soil chemistry in carpet applications. The method requires a known amount of FI trace to be added along with anti-soil chemistry in formulation prior to application to a carpet surface. The anti-soil chemistry with the trace amount of FI is then applied to the carpet through a topical foam or spray applicator during a precoating process. After completion of the precoat process, a carpet sample is collected, carpet face fiber is isolated, preferably by shaving, and FI is extracted, preferably using a water extraction process. The extracted water solution is used to measure the emission intensity (in counts per second or "CPS") using a Fluorimeter. The measured FI may then be compared to an expected FI baseline to determine the degree of successful application of the anti-soil chemistry to carpet face fiber. The parameters of the application process itself, including speed, pressure, temperature, application mechanism and/or concentration may then be adjusted based on the results of the quantitative measurement of the invention in order to achieve the desired degree of application. It is noted that while the method is generally intended for non-fluorine chemistry, it can be used for fluorine-containing chemistry as well, so long as the emission spectrum for the particular FI molecule employed does not interfere with that of the applied chemistry.

BRIEF DESCRIPTION OF THE DRAWINGS

FIG. 1 shows pure fluorescent indicator (FI) (10 ppm) at 1 nm slit; FIG. 2 shows emission of water sample extracted from carpet sample treated with 25 ppm FI, which is further diluted to 0.75 ppm by dissolving 1 gram of shaved fiber in 20 mL water.

DETAILED DESCRIPTION

Figure 1:
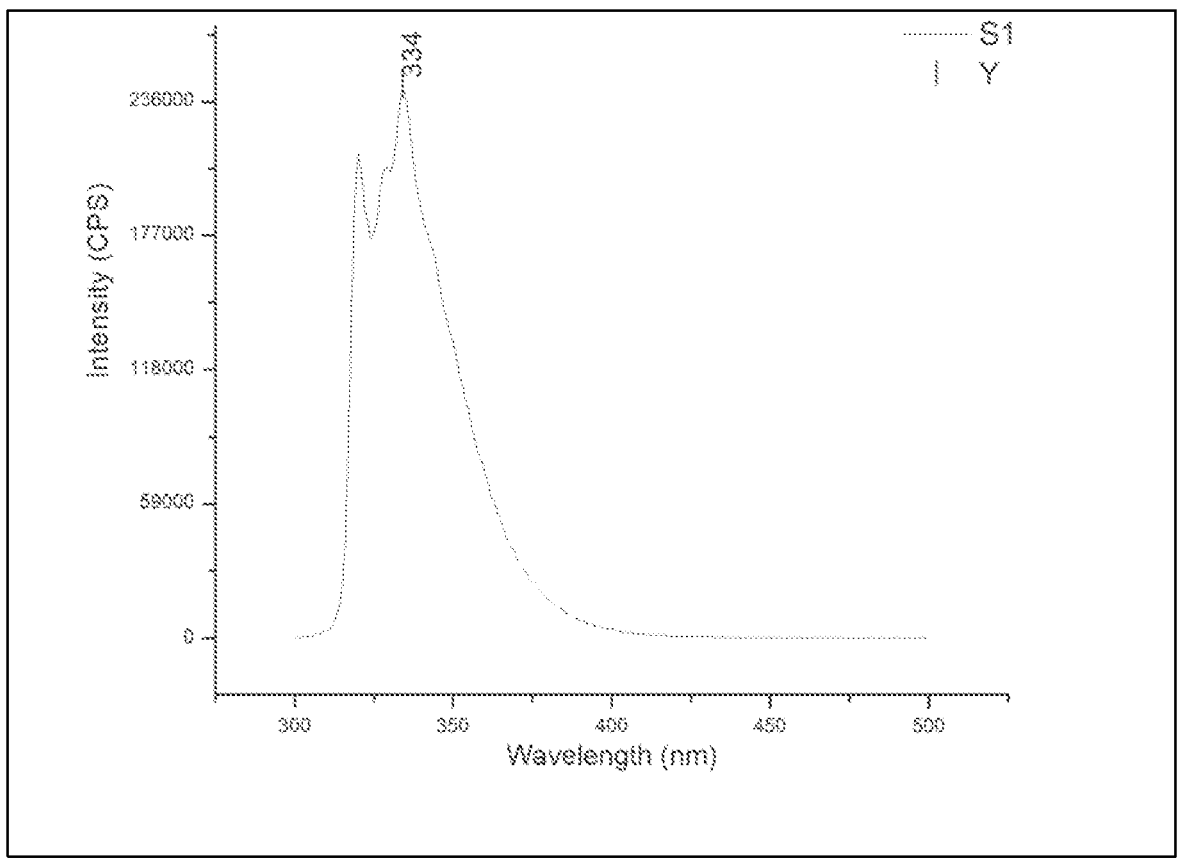
FIGS. 1 and 2: show Fluorescence Emission Spectra of Pure and Extracted Samples in Example 1.

As used herein, a "trace amount" refers to an average concentration of less than or equal to 100 parts per million (ppm) of anti-soil coating solution, preferably about 5-100 ppm.

The inventors have developed a novel, cost-effective, quantitative, test method that can be used to measure non-fluorine anti-soil chemistry in carpet applications. This method will help manufacturing detect and monitor anti-soil application rate with more consistency and provide better quality control. In addition, this method can be used beyond anti-soil application and testing. For example, the method can be used with a manufacturing process, such as in material coating or compounding, where the material application rate cannot otherwise be measured and monitored directly using the processing materials. In particular, the method is particularly directed toward surfaces having an irregular and/or three-dimensional surface, such as woven textile, and particularly carpeting. In addition to the irregularity of a carpet surface, the nature of the carpet face fiber design makes it inherently difficult to measure the degree of application of a chemical layer applied thereto.

The method requires a known amount of FI trace be added along with anti-soil chemistry in formulation, which is then applied to the carpet (in one embodiment, by way of a known topical foam applicator) during a topical/spray treatment process. After completion of the topical/spray process, a carpet sample is collected, carpet face fiber is isolated and removed (e.g. by shaving), and FI is extracted using water at alkaline pH of about 8.5-9.5, preferably of about 9 More specifically, in one embodiment, one gram of shaved fiber is added to 19 mL of de-ionized water along with 1 mL of 1% sodium carbonate, followed by agitation for 30 minutes. The extraction process, amounts and timing may be adjusted according to the knowledge of one skilled in the art. The extracted water solution is filtered and used to measure the emission intensity using a Fluorimeter. The fluorescence emission intensity is directly proportional to the concentration of FI on the carpet fiber. Hence, the concentration of anti-soil is measured indirectly. The general principle is that the FI absorbs light at a lower UV-region (228 nm) and emits light in the higher UV-region (334 nm). The fluorescence emission intensity is measured to quantify the amount of FI trace, i.e., indirectly providing the concentration of anti-soil compound as applied to the carpet face. Remarkably, the FI provides emission in the non-visible UV-region and will not impact the carpet color aesthetics.

The Fluorescent Indicator (FI)

The Fluorescent compounds may generally comprise a naphthalic, pyrene or phenyl moiety having the following general chemical structure:

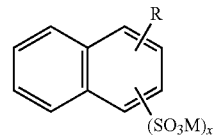

where R is an amino (—NH2), hydroxyl (—OH) group, aliphatic, aromatic, alicyclic, alkyl (straight or branched chain), phenyl, halogen, heteroaromatic moiety at any position of naphthalene ring; similarly X is sulfonic acid or its salt with an integer from 0-3 may be attached at any position of naphthalene moiety; and M is sodium, potassium or lithium metal. Examples of FI that may be suitable include, but are not limited to 1,5-Naphthalenedisulfonic acid disodium salt; 1,5-Naphthalenedisulfonic acid tetrahydrate; 2,6-Naphthalenedisulfonic acid disodium salt; 1-Naphthol-4-sulfonic acid sodium salt; 6-Hydroxy-2-naphthalenesulfonic acid sodium salt hydrate; 2-naphthol-6-sulfonic acid potassium salt; 2-Naphthol-3,6-disulfonic acid disodium salt; 4-Hydroxy-2,7-naphthalenedisulfonic acid disodium salt; 4-Amino-5-hydroxynaphthalene-2,7-disulfonic acid monosodium salt hydrate; Tetrasodium 1,3,6,8-pyrenetetrasulfonate hydrate; 1-Pyrenesulfonic acid sodium salt and 8-Hydroxypyrene-1,3,6-trisulfonic acid trisodium salt. In a particular embodiment, the FI is 1,5-Naphthalenedisulfonic acid disodium salt (CAS Number 1655-29-4).

Anti-Soil Composition

The inventive test method can be used to measure the effective application level of any coating material to a textile surface. In one embodiment, the method is used to measure the effective application of anti-soil materials such as fluorochemicals, acrylics, silicones and waxes materials on a textile and/or carpet surface, which may be woven, tufted or non-woven.

Coatings Systems

The inventive test method can be used with any polymer/material coating systems where the polymer/material application rate needs to quantify. Examples of coating systems that may be suitable include, but are not limited to, carpet anti-soil coatings, textile water-repellant coatings and textile softening coatings.

Alternatives

A rare metal trace can be used as an indicator, but it may be less desirable because of its associated lower solubility and stability.

Finally, it should be clear to those skilled in the art that each embodiment disclosed herein can be and is contemplated as being applicable to each of the other disclosed embodiments. Accordingly, all combinations of the various elements described herein are within the scope of the invention.

EXPERIMENTAL DETAILS

Example 1

The objective of this experiment is to develop a cost-effective, quantitative test method to measure non-fluorine anti-soil chemistry application rate in a topical/spray using a FI. This experiment involves screening and evaluating fluorescent trace agents that can be used as an indicator to monitor the anti-soil application rate using a Fluorimeter, in carpet topical/spray application.

Fluorescent Indicator (FI) Application Rate

Preparation of 1000 ppm FI Stock Solution

Fluorescent Indicator (FI)=0.100 grams (1,5-Naphthalenedisulfonic acid disodium salt (CAS Number 1655-29-4))

Eco-Ensure (Anti-soil mix/Solution)=100 mL

TABLE 1

Preparation of Eco-Ensure and Fluorescent Indicator solution (mix) and application rate to four carpet samples (based on dilution with additional Eco-Ensure solution)

| Sample | FI, Concentration (PPM) | Carpet sample weight (grams) | Calculated Eco-Ensure mix application rate (grams) | Actual Eco-Ensure mix application rate* (grams) |
|---|---|---|---|---|
| Blank | 0 | 50 | 11 | 12.0 |
| A | 25 | 50 | 11 | 11.9 |
| B | 25 | 50 | 11 | 11.7 |
| C | 25 | 50 | 11 | 11.3 |

*The amount of Eco-Ensure mix is calculated and used based on 22% wet pick-up and 2% Eco-Ensure add-on (target) on the weight of carpet face fiber.

TABLE 2

Fluorescent Indicator (FI) Extraction Method from Carpet Samples

| Fiber wt. | 1 | gram |
|---|---|---|
| Water | 19 | mL |
| Sodium Carbonate (1%) | 1 | mL |
| pH | 9 ± 0.5 | |
| Agitation | 30 | minutes |

TABLE 3

Fluorescence Emission Measurement to effectiveness of FI extrusion process.

| Sample | Concentration (PPM) | Fiber wt. (grams) | Excitation λ (nm) | Emission λ (nm) | Emission Intensity (CPS) |
|---|---|---|---|---|---|
| Blank sample | 0 | 1.0036 | 280 | 334 | No peak |
| 1st extraction, sample A | 25 | 1.0054 | 280 | 334 | 632710 |
| 1st extraction, sample B | 25 | 1.0065 | 280 | 334 | 711760 |
| 1st extraction, sample C | 25 | 1.0087 | 280 | 334 | 644540 |
| 2nd extraction, sample A | NA | 1.0054 | 280 | 334 | 103500 |
| 2nd extraction, sample B | NA | 1.0065 | 280 | 334 | 109740 |
| 2nd extraction, sample C | NA | 1.0087 | 280 | 334 | 110440 |
| 3rd extraction, sample A | NA | 1.0054 | 280 | 334 | 28370 |
| 3rd extraction, sample B | NA | 1.0065 | 280 | 334 | 23420 |
| 3rd extraction, sample C | NA | 1.0087 | 280 | 334 | 21350 |

Measurement conditions: slit = 2 nm; increment = 1 nm and filtered Ext. Solu. = PA, 0.45 μm.

Figure 2:
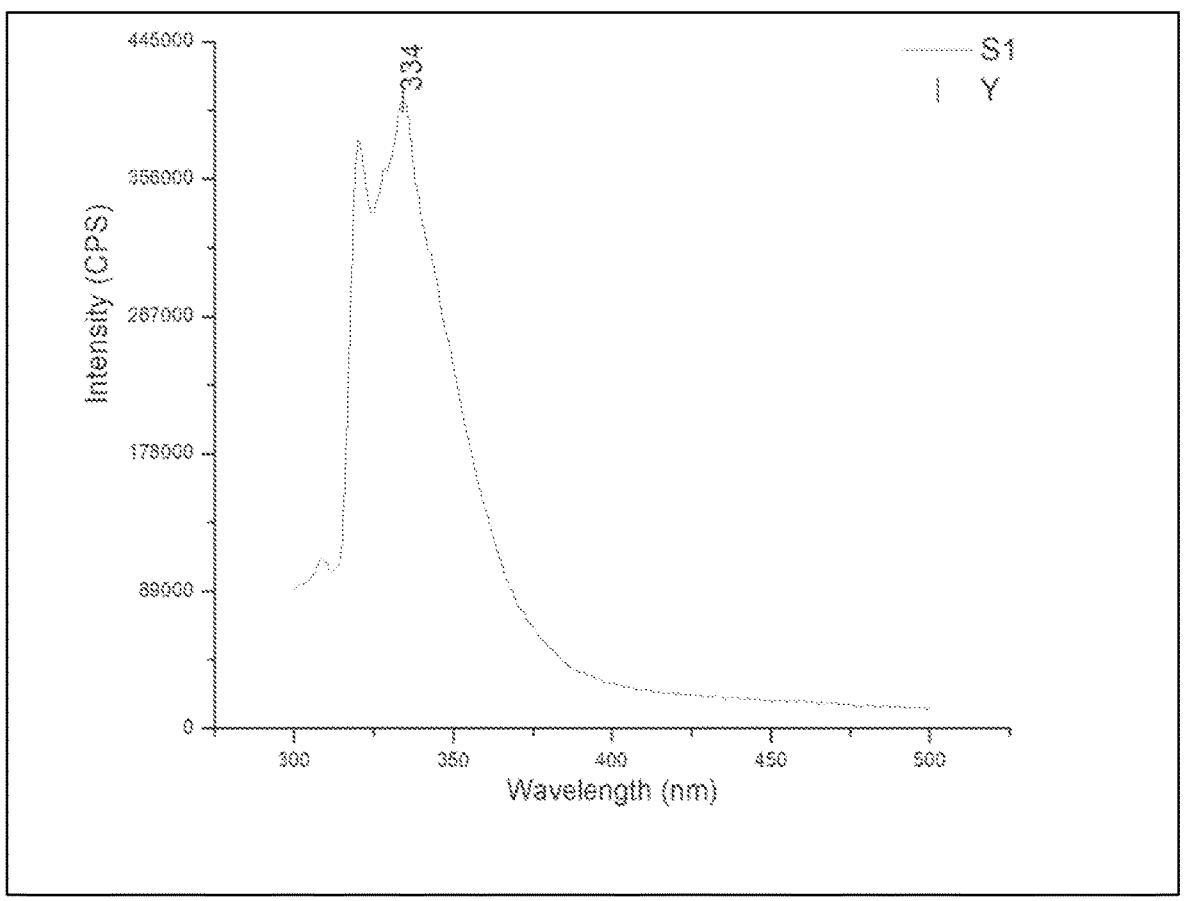

Emission spectra of pure FI in de-ionized water at 10 ppm concentrations are shown in FIG. 1 Fluorescence emission intensity of pure FI after extraction from carpet fiber treated with a 25 ppm solution of FI is shown in FIG. 2. Emission spectrum of fluorescent trace indictor sample extracted from carpet fiber is measured in deionized water. The carpet sample was treated with 25 ppm fluorescent indicator and Eco-Ensure mix using a foam applicator at a wet-pickup of 22%.

Figure 3:
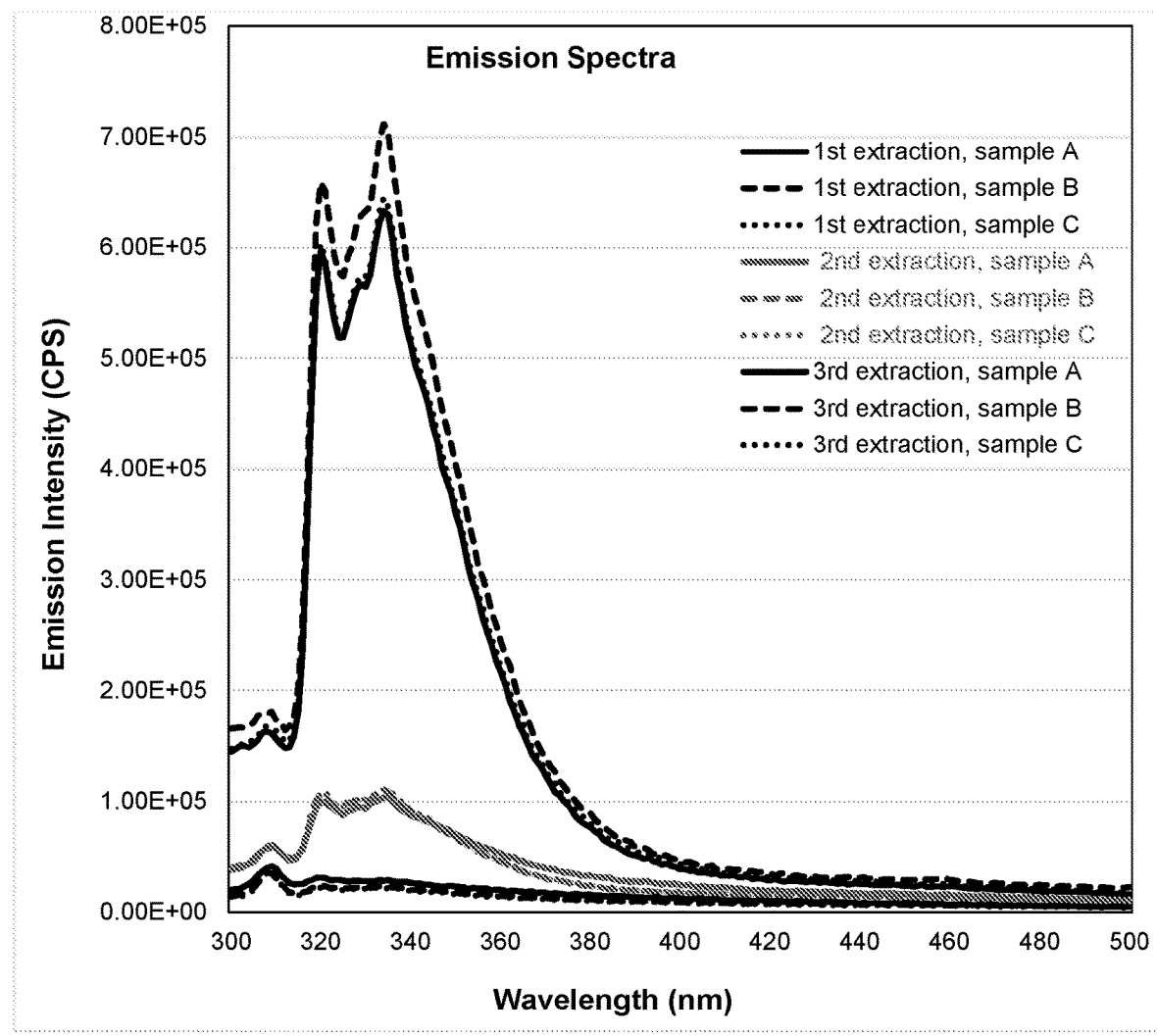
FIG. 3: shows Emission Spectra at Various extraction in Example 1.

Fluorescence Emission Spectra of FI extracted from carpet fiber samples are shown in FIG. 3. The 25 ppm trace amount of FI along with Eco-Ensure anti-soil is applied to the carpet through a topical foam applicator during a precoat process, carpet face fiber is isolated by shaving, using 1 g fiber from each of three samples A-C and FI is extracted using a 20 mL water extraction process. The extraction process is repeated three times for each sample and emission is measured each time (in counts per second or "CPS") using a Fluorimeter) to evaluate effectiveness of the extrusion process. The extraction result showed that the FI indicator is rapidly soluble in water and effectively removed from the fiber in first extrusion. The residual FI in second extrusion is very minimum and in third extrusion it is completely removed.

Figure 4:
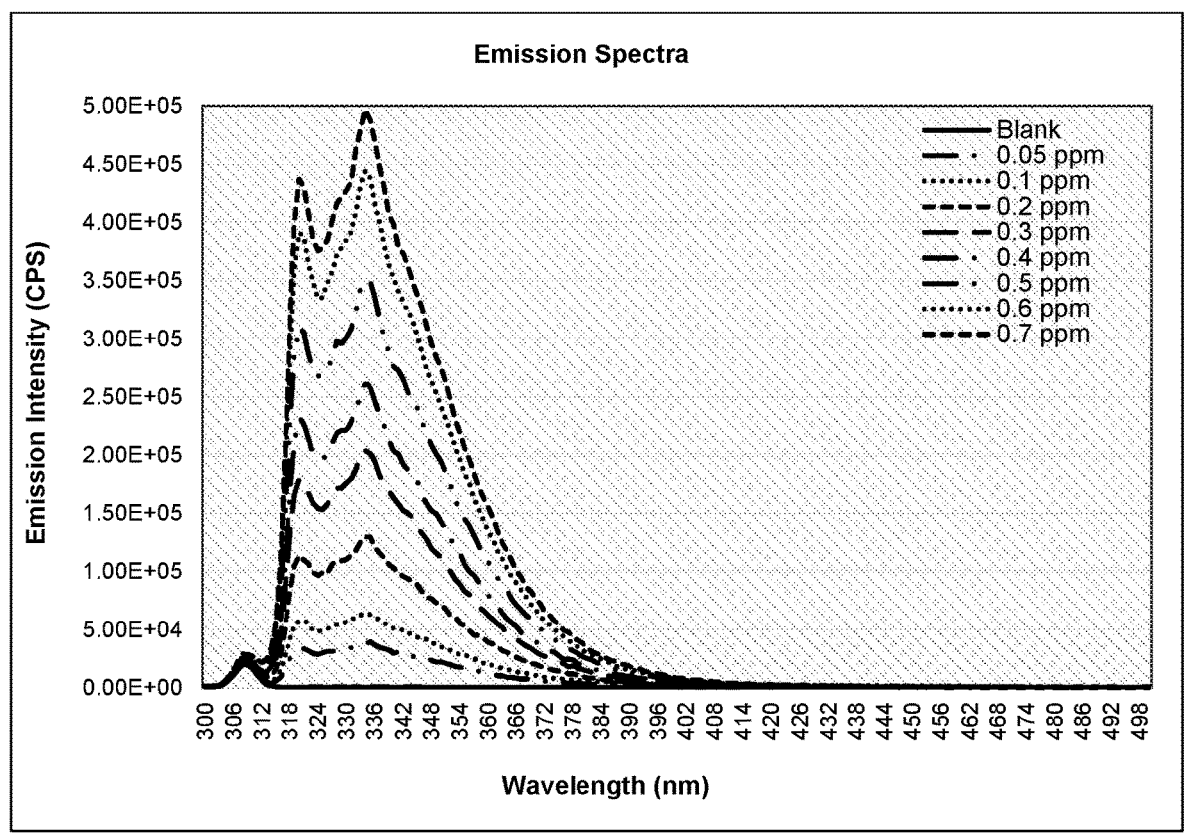
FIGS. 4 and 5 show pure FI at various concentrations to determine the emission baseline.
Figure 5:
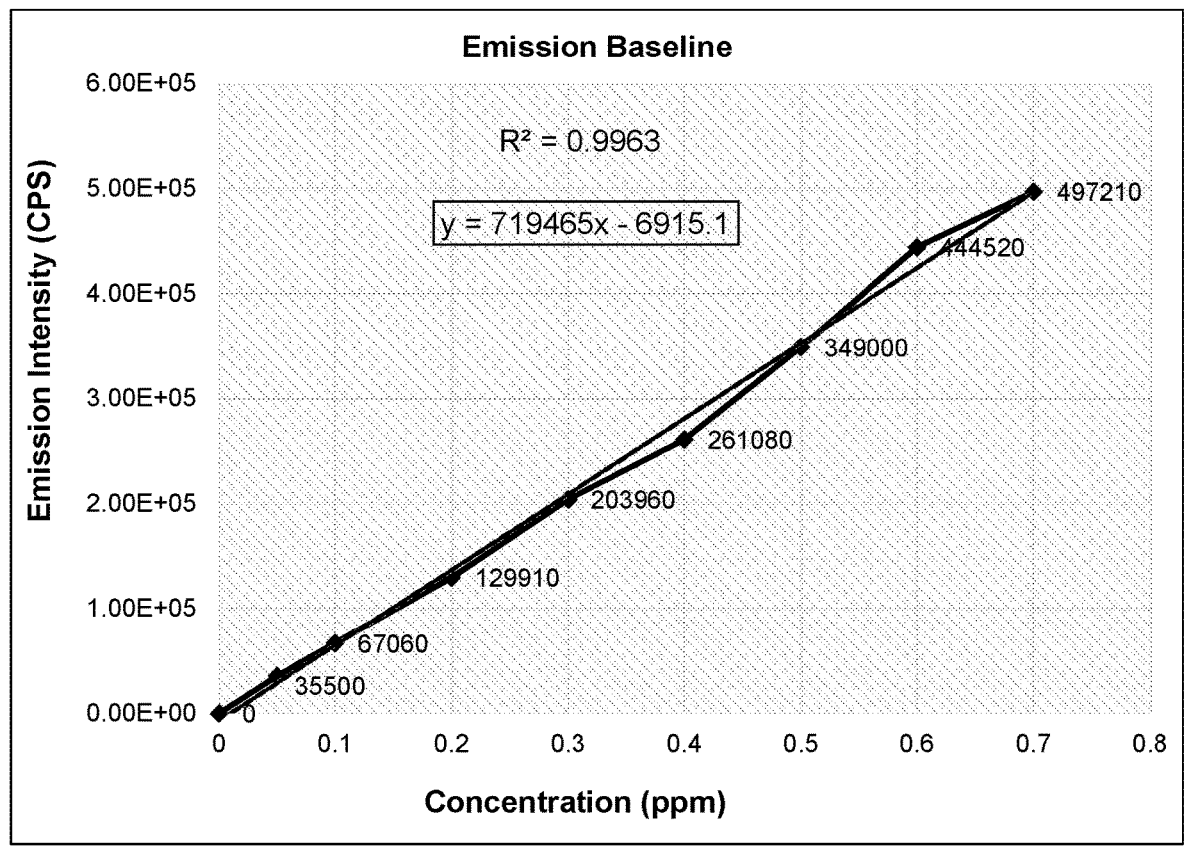

In order to have a comparative baseline measurement for presence of FI indicator, emission intensity was measured for the FI indicator in pure water solution based on varying amounts of FI indicator. The results are set out in Table 5 below where a direct correlation between amount of FI and measured intensity is seen. FIG. 4 shows the corresponding emission spectra and FIG. 5 depicts the baseline graphically.

TABLE 4

Fluorescent Indicator concentration in pure water solution and their emission intensity for baseline measurements

| Sample # | Fluorescent Indicator Concentration (ppm) | Excitation λ (nm) | Emission λ (nm) | Emission Intensity (CPS) |
|---|---|---|---|---|
| 1 | Blank | 280 | 334 | 570 |
| 2 | 0.05 | 280 | 334 | 35500 |
| 3 | 0.1 | 280 | 334 | 67060 |

TABLE 4-continued

Fluorescent Indicator concentration in pure water solution
and their emission intensity for baseline measurements

| Sample # | Fluorescent Indicator Concentration (ppm) | Excitation λ (nm) | Emission λ (nm) | Emission Intensity (CPS) |
|---|---|---|---|---|
| 4 | 0.2 | 280 | 334 | 129910 |
| 5 | 0.3 | 280 | 334 | 203960 |
| 6 | 0.4 | 280 | 334 | 261080 |
| 7 | 0.5 | 280 | 334 | 349000 |
| 8 | 0.6 | 280 | 334 | 444520 |
| 9 | 0.7 | 280 | 334 | 497210 |

A preferred ratio of Fluorescent Indicator and Eco-Ensure anti-soil was used in testing formulation in connection with Table 5 to prepare the topical anti-soil treatment solution, which is employed to carpet face fiber using a foam applicator during precoat process.

TABLE 5

Preoaration of Eco-Ensure and Fluorescent
Indicator solution and their weight ratio

| Anti-soil treatment chemical formulation | Concentration (wt %) | Concentration (ppm) | weight ratio (Eco-Ensure/Indicator) |
|---|---|---|---|
| Eco-Ensure | 9 | 90000 | 1800 |
| Fluorescent Indicator | 0.01 | 50 | |

TABLE 6A

The Eco-Ensure and FI treat carpet fiber weight
and emission intensity test results

| Sample # | Shaved fiber weight (g) | Deionized water (dilution) mL | Excitation λ (nm) | Emission λ (nm) | Emission Intensity (CPS) |
|---|---|---|---|---|---|
| 1 | 1.014 | 20 | 280 | 334 | 493540 |
| 2 | 1.014 | 20 | 280 | 334 | 466600 |
| 3 | 1.024 | 20 | 280 | 334 | 528590 |
| 4 | 1.020 | 20 | 280 | 334 | 462080 |
| 5 | 1.015 | 20 | 280 | 334 | 436200 |
| 6 | 1.030 | 20 | 280 | 334 | 462770 |
| 7 | 1.025 | 20 | 280 | 334 | 410810 |
| 8 | 1.029 | 20 | 280 | 334 | 482370 |
| 9 | 1.024 | 20 | 280 | 334 | 481050 |
| 10 | 1.025 | 20 | 280 | 334 | 491460 |
| 11 | 1.027 | 20 | 280 | 334 | 504780 |
| 12 | 1.027 | 20 | 280 | 334 | 446450 |
| 13 | 1.023 | 20 | 280 | 334 | 446180 |
| 14 | 1.030 | 20 | 280 | 334 | 477960 |
| 15 | 1.026 | 20 | 280 | 334 | 448540 |
| 16 | 1.030 | 20 | 280 | 334 | 487380 |
| 17 | 1.034 | 20 | 280 | 334 | 503070 |
| 18 | 1.032 | 20 | 280 | 334 | 521460 |
| 19 | 1.029 | 20 | 280 | 334 | 483120 |
| 20 | 1.027 | 20 | 280 | 334 | 496880 |
| 21 | 1.024 | 20 | 280 | 334 | 440860 |

TABLE 6B

Estimation of % Eco-Ensure amount on carpet
fiber using FI emission test results

| Sample # | Emission Intensity (CPS) | ppm, F. Indicator (y = 719465x − 6915.1) | Ratio (Eco-Ensure/Indicator) | ppm, Eco-Ensure (ppm-Ind. × 1800 × 20@) | % Eco-Ensure on weight of carpet fiber |
|---|---|---|---|---|---|
| 1 | 493540 | 0.611 | 1800 | 21985.54 | 2.20 |
| 2 | 466600 | 0.578 | 1800 | 20802.04 | 2.08 |
| 3 | 528590 | 0.653 | 1800 | 23525.33 | 2.35 |
| 4 | 462080 | 0.572 | 1800 | 20603.47 | 2.06 |
| 5 | 436200 | 0.541 | 1800 | 19466.53 | 1.95 |
| 6 | 462770 | 0.573 | 1800 | 20633.78 | 2.06 |
| 7 | 410810 | 0.51 | 1800 | 18351.12 | 1.84 |
| 8 | 482370 | 0.597 | 1800 | 21494.83 | 2.15 |
| 9 | 481050 | 0.595 | 1800 | 21436.84 | 2.14 |
| 10 | 491460 | 0.608 | 1800 | 21894.17 | 2.19 |
| 11 | 504780 | 0.624 | 1800 | 22479.33 | 2.25 |
| 12 | 446450 | 0.553 | 1800 | 19916.83 | 1.99 |
| 13 | 446180 | 0.553 | 1800 | 19904.97 | 1.99 |
| 14 | 477960 | 0.592 | 1800 | 21301.1 | 2.13 |
| 15 | 448540 | 0.556 | 1800 | 20008.64 | 2.00 |
| 16 | 487380 | 0.603 | 1800 | 21714.93 | 2.17 |
| 17 | 503070 | 0.622 | 1800 | 22404.21 | 2.24 |
| 18 | 521460 | 0.645 | 1800 | 23212.1 | 2.32 |
| 19 | 483120 | 0.598 | 1800 | 21527.78 | 2.15 |
| 20 | 496880 | 0.615 | 1800 | 22132.27 | 2.21 |

@= Dilution Factor, one gram of shaved fiber is added to 20 mL of de-ionized water to extract fluorescent indicator The confirmation data as set forth in Table 6 above shows that the test measurement provides verifiable confirmation of the degree of anti-soil application on carpet fibers, in this case in reference to a desired application rate of 2% Eco-Ensure. The results indicate a mean rate of application at 2.11%+/−0.13.

What is claimed is:

1. A method for quantitatively measuring an amount of a non-fluorine anti-soil treatment composition present on a textile substrate, the method comprising the following steps, in order:
    (a) adding a predetermined amount of a fluorescent indicator (FI) of 1,5 naphthalenedisulfonic acid disodium salt to the non-fluorine anti-soil treatment composition;
    (b) applying the non-fluorine anti-soil treatment composition obtained from (a) to a surface of the textile substrate;
    (c) collecting a sample from the surface of the textile substrate;
    (d) extracting the FI from a portion of the collected sample to obtain a solution containing the extracted FI;
    (e) measuring a fluorescence emission intensity in the solution containing the extracted FI, and
    (f) comparing the measured fluorescence emission intensity to a predetermined baseline determine a concentration of FI indicative of a degree of application of the non-fluorine anti-soil treatment composition to the portion of the collected sample.

2. The method of claim 1, wherein (c) further comprises isolating the sample of the textile substrate and removing the portion of the surface from the sample.

3. The method of claim 1, wherein the textile substrate is a carpet.

4. The method of claim 1, wherein the textile substrate has an uneven and/or irregular surface onto which the treatment composition is applied.

5. The method of claim 1, wherein the predetermined amount of the FI in (a) is between 5-100 ppm of FI.

6. The method of claim 1, wherein, in (b), the non-fluorine anti-soil treatment composition is applied using a topical foam applicator.

7. A method for quantitatively measuring an amount of a non-fluorine anti-soil treatment composition present on a textile substrate, the method comprising the following steps, in order:
(a) adding a predetermined amount of a fluorescent indicator (FI) of 1,5 naphthalenedisulfonic acid disodium salt to the non-fluorine anti-soil treatment composition;
(b) applying the non-fluorine anti-soil treatment composition obtained from (a) to a surface of the textile substrate;
(c) collecting a sample from the surface of the textile substrate, wherein the collected sample comprises at least one face fiber;
(d) isolating the at least one face fiber from the collected sample;
(e) extracting the FI from the isolated at least one face fiber to obtain a solution containing the extracted FI;
(f) measuring the fluorescence emission intensity in the solution containing the extracted FI;
(g) comparing the measured fluorescence emission intensity to a predetermined baseline to determine a first degree of application of the non-fluorine anti-soil treatment composition to the isolated at least one face fiber; and
(h) adjusting one or more parameters of an application or manufacturing process based on the determined first degree of application such that a second degree of the non-fluorine anti-soil treatment composition is applicable to another textile substrate via the adjusted one or more parameters of the application or manufacturing process, wherein the determined first degree of application is a greater degree of application or lesser degree of application than the second degree of application.

8. The method of claim 1, wherein the one or more parameters comprise at least one of speed, pressure, temperature, application mechanism, and concentration.

9. A method for quantitatively measuring an amount of a non-fluorine anti-soil treatment composition present on a textile substrate, the method comprising the following steps, in order:
(a) adding a predetermined amount of a fluorescent indicator (FI) to the non-fluorine anti-soil treatment composition;
(b) applying the non-fluorine anti-soil treatment composition obtained from (a) to a surface of the textile substrate;
(c) collecting a sample of the surface;
(d) extracting the FI from a fiber portion of the collected sample to obtain a solution containing extracted FI;
(e) measuring the fluorescence emission intensity in the solution containing extracted FI; and
(f) comparing the measured fluorescence emission to a predetermined baseline to determine a concentration of FI with respect to the fiber portion of the collected sample,
wherein the FI comprises a naphthalic, pyrene, or phenyl moiety having the chemical structure:

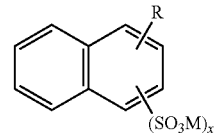

wherein
R is an amino (—NH2), hydroxyl (—OH) group, aliphatic, aromatic, alicyclic, alkyl (straight or branched chain), phenyl, halogen, or heteroaromatic moiety at any position of naphthalene ring,
X is sulfonic acid or its salt with an integer from 0-3 attached at any position of naphthalene moiety, and
M is sodium, potassium, or lithium metal.

* * * * *